(12) United States Patent
Whitelaw et al.

(10) Patent No.: US 7,435,555 B2
(45) Date of Patent: Oct. 14, 2008

(54) ASPARAGINE HYDROXYLATION OF THE CAD DOMAIN OF A HIF PROTEIN

(75) Inventors: Murray L Whitelaw, Brighton (AU); David Lando, Cambridge (GB); Daniel J Peet, Panorama (AU); Jeffrey J Gorman, Fig Tree Pocket (AU); Sarah Linke, Myrtle Bank (AU)

(73) Assignee: Adelaide Research and Innovation Pty Ltd., Adelaide, South Australia (AU)

( * ) Notice: Subject to any disclaimer, the term of this patent is extended or adjusted under 35 U.S.C. 154(b) by 280 days.

(21) Appl. No.: 10/490,085

(22) PCT Filed: Sep. 18, 2002

(86) PCT No.: PCT/AU02/01290

§ 371 (c)(1),
(2), (4) Date: Sep. 16, 2004

(87) PCT Pub. No.: WO03/025013

PCT Pub. Date: Mar. 27, 2003

(65) Prior Publication Data

US 2005/0064533 A1     Mar. 24, 2005

(30) Foreign Application Priority Data

Sep. 18, 2001   (AU) .................................... PR7738

(51) Int. Cl.
*C12Q 1/00*   (2006.01)
*C12Q 1/16*   (2006.01)
*C12Q 1/68*   (2006.01)

(52) U.S. Cl. ............................. 435/7.5; 435/6; 530/300; 424/1.65

(58) Field of Classification Search ........................ None
See application file for complete search history.

(56) References Cited

OTHER PUBLICATIONS

Linke et al., "Substrate requirements of the oxygen-sensing asparaginyl hydroxylase factor-inhibiting hypoxia-inducible factor", Journal of Biological Chemistry 279: 14391-14397 (2004).*

Hewitson, Kirsty S. et al., "Hypoxia-inducible Factor (HIF) Asparagine Hydroxylase is Identical to Factor Inhibiting HIF and is Related to the Cupin Structural Family," J. of Biological Chemistry (Jul. 19, 2002) 277 (29) pp. 26351-26355.

William, Carsten et al., "Peptide blockade of HIF α degradation modulates cellular metabolism and angiogenesis," Proceedings of the Nat. Acad. of Sci. of the United States of America (Aug. 6, 2002) 99 (16) pp. 10423-10428.

Groulx, Isabelle et al., "Oxygen-Dependent Ubiquitination and Degradation of Hypoxia-Inducible Factor Requires Nuclear-Cytoplasmic Trafficking of the von Hippel-Lindau Tumor Suppressor Protein," Molecular and Cellular Bio., (Aug. 2002) 22 (15) pp. 5319-5336.

Dames, Sonja A. et al., "Structural basis for Hif-1α/CBP recognition in the cellular hypoxic response," Proceedings of the Nat. Acad. of Sci. of the United States of America (Apr. 16, 2002) 99 (8) pp. 5271-5276.

Jaakola, P. et al., "Targeting of HIF-α to the von Hippel-Lindau Ubiquitylation Complex by $O_2$-Regulated Prolyl Hydroxylation," Science (Apr. 20, 2001) 292 (5516) pp. 468-472.

* cited by examiner

*Primary Examiner*—Robert B. Mondesi
*Assistant Examiner*—Anand U. Desai
(74) *Attorney, Agent, or Firm*—Henry D. Coleman; R. Neil Sudol; William J. Sapone

(57) ABSTRACT

A target asparagine residue of HIF 1 alpha and 2 alpha is hydroxylated at high oxygen tension to render HIF as a weak transcription factor. An asparagine hydroxylase hydroxylation motif and binding motif is proposed. A method of screening for agonists or antagonists of an asparagine hydroxylase is also proposed and involves mixing peptides or proteins having the hydroxylation and or the binding motif with asparagine hydroxylase and a candidate agonist or antagonist. The extent of inhibition or enhancement of binding; level of asparagine hydroxylation or transactivation may be measured depending on the nature of the protein or peptide. Additionally altered proteins resistant to hydroxylation are described as are nucleic acids encoding such proteins.

15 Claims, 10 Drawing Sheets

A

B   C

A

```
mHIF-2α (844-860)    TRYDCEVNVPVPGSSTL
hHIF-2α (840-856)    TRYDCEVNVPVLGSSTL
rHIF-2α (844-860)    TRYDCEVNVPEPGSSTL
mHIF-1α (796-812)    TSYDCEVNAPIQGSRNL
hHIF-1α (796-812)    TSYDCEVNAPIQGSRNL
rHIF-1α (795-811)    TSYDCEVNAPIQGSRNL
```

ASPARAGINE HYDROXYLATION OF THE CAD DOMAIN OF A HIF PROTEIN

FIELD OF THE INVENTION

This invention relates to an altered HIF protein having modified asparagine hydroxylase binding and hydroxylation motifs, proteins or peptides exhibiting such modified motifs, nucleic acids encoding such modified motifs and cells carrying such nucleic acids. Additionally the invention relates to a method of isolating agonists or antagonists of hydroxylation of the asparagine hydroxylation of HIP.

BACKGROUND OF THE INVENTION

Normal human physiology is dependent upon a continual supply of oxygen. When oxygen becomes limiting, cells of affected tissues undergo a number of adaptive responses to aid survival. These include metabolic adjustments, for example, switching energy production from oxidative phosphorylation to glycolysis, as well as genetic reprogramming events aimed at increasing oxygen supply to tissues. Key genes which are activated during hypoxia (low oxygen stress) include those which encode erythropoietin (EPO), a growth factor which increases the production of oxygen carrying red blood cells; Vascular Endothelial Growth Factor (VEGF), a protein which promotes new blood vessel development; and a set of genes which produce enzymes involved in glycolysis as well as a number of other changes.

A number of oxygen sensitive mediators have been identified. Two proteins which sense depleted oxygen levels and subsequently act as transcription factors (gene regulatory factors) to induce the above mentioned genes are the Hypoxia Inducible Factors 1α and 2α (HIF-1α and HIF-2α).

HIF-1α and HIF-2α are two closely related transcription factors. The schematic of FIG. 1 shows these proteins exhibit a similar organisation of functional domains. The N-terminal bHLH/PAS domains are important for dimerisation and DNA binding; the Oxygen Dependent Degradation Domains (ODDs) mediate protein turnover; and the C-terminal transactivation domains (CADs) are important for inducing transcription of target genes.

Both the ODD and CAD domains of each protein are known to sense depleted cellular oxygen levels. The ODDs confer extreme lability to the HIF-1α and HIF-2α proteins. At normoxia (20% atmospheric oxygen), the proteins are so labile that they are effectively absent from most cell types when analysed by antibodies. In contrast, when cells are subjected to hypoxia (<2% oxygen) the HIF proteins are stable and readily detected with antibodies. Recently, the mechanism by which the ODDs sense oxygen was elucidated (Zhu and Bunn, 2001; Ivan et al., 2001; Jaakkola et al., 2001). At normal oxygen levels, an oxygen and $Fe^{2+}$ dependent prolyl hydroxylase enzyme is responsible for hydroxylating a conserved proline residue within the ODDs. The hydroxyproline is required for connecting HIF-1α and HIF-2α to the von-Hippel Lindau factor (VHL). VHL is part of a protein complex that initiates addition of ubiquitin chains to the HIF substrate proteins, subsequently targeting the HIFs to the protein degrading proteasome. During hypoxia, the oxygen dependent prolyl hydroxylase does not function and the critical proline in the ODDs remains unmodified. This allows the HIF proteins to avoid VHL surveillance and escape the proteasome degradation machinery (FIG. 2).

During hypoxia, HIF-1α and HIF-2α become stable proteins and function as transcription factors, that is, they trigger induction of target genes such as EPO and VEGF. The ability to induce target genes relies on transactivation domains, which are responsible for connecting the DNA bound HIF proteins to the transcription machinery of the cell. Two distinct transactivation domains exist within HIF-1α and HIF-2α. One is ill defined and intrinsic to the ODD, while the other is at the C-terminus (CAD) and represents a second domain which is capable of responding to hypoxia. The CADs of HIF-1α and HIF-2α are the dominant transactivation domains and respond to hypoxia in a manner which is independent of protein stability. The importance of the CAD from HIF-1α is exemplified by disruption of its function in mice. In these experiments, ectopic expression of CAD peptides resulted in attenuation of hypoxia induced genes and a reduction in growth of induced tumours (Kung et al., 2000).

There are several documents that describe some aspects of the behaviour of the CAD domain of HIF in normoxic conditions compared to hypoxic conditions however none of these has identified the hydroxylation of a target asparagine (O'Rourke et al., 1999, Ema et al., 1999, Carerro et al., 2000, Gu et al., 2001, Jiang et al., 1997). The term CAD refers to a functional transactivation domain at the C-terminus of the HIF-1α and HIF-2α proteins and different laboratories use the term to describe varying lengths of the C-terminus. We define the CAD as the hypoxia inducible C-terminal transactivation domain contained within the last 100 amino acids of HIF-1α and HIF-2α.

SUMMARY OF THE INVENTION

This invention arises from the finding that a target asparagine residue of HIF 1α and 2α is hydroxylated at high oxygen tension, to thereby render HIF as a weak transcription factor. Additionally other amino acids of the HIF protein have been identified as being important in hydroxylation of the target asparagine.

The target asparagine that is subject of the hydroxylation occurs within a motif that is conserved as between HIF 1α and 2α as well as between mouse and human. An hydroxylation motif adjacent the hydroxylated asparagine is also highly conserved and seems likely to be important in the hydroxylation. O'Rourke et al., (1999) also found that alteration of the amino acid triplet RLL at positions 774-776 in HIF-1α are essential for oxygen modulation of the transactivation function of HIF-1α. Similarly adjacent amino acids are highly conserved and it is proposed that these constitute a binding motif, and that alteration in these will interfere with the action of the asparagine hydroxylase. It is found that the RLL sequence is critical for the binding of the asparagine hydroxylase to the CAD domain in pull-down assays.

The invention might in a first broad aspect be said to reside in a DNA binding protein having an altered HIF CAD domain, whereby the alteration inhibits hydroxylation of the asparagine but maintains the capacity of the altered CAD domain to exert its transactivation function the HIF CAD domain preferably exhibiting an altered hydroxylation motif.

The invention might in a second broad aspect be said to include a purified nucleic acid sequence, or recombinant molecule encoding an altered DNA binding protein or HIF protein encoding the above altered protein, or such a nucleic acid sequence carried in a vector. Another aspect of the invention encompasses recombinant cells carrying DNA into which the above nucleic acid has been introduced.

A third aspect of the invention encompasses a method of screening for antagonists of the asparagine hydroxylase, or the asparagine hydroxylase by the capacity of candidate molecules to bind either a wild type HIF CAD domain or the asparagine hydroxylase binding motif or hydroxylation motif or binding to the asparagine hydroxylase.

A fourth aspect of the invention might be said to reside in a method of screening for agonists or antagonists of the asparagine hydroxylase, which involves using a preparation containing the asparagine hydroxylase, and a HIF CAD domain or portion thereof, adding a candidate agonist or antagonist, and detecting inhibition or enhancement of hydroxylation of the target asparagine.

Whilst it is not anticipated that there will be an asparagine dehydroxylase because the turnover of HIF-1α and HIF-2α is quite high, there is a prospect that such a molecule exists. The invention also therefore in a sixth aspect encompasses a method of screening for the presence of a putative asparagine dehydroxylase by screening for binding of candidate molecules against hydroxylated CAD domain or fragments thereof, or to the asparagine hydroxylase binding and/or hydroxylation motif.

DETAILED DESCRIPTION OF THE INVENTION

By way of a shorthand notation the following three and one letter abbreviations for amino acid residues are used in the specification as defined in Table 1.

Where a specific amino acid residue is referred to by its position in the polypeptide of a protein, the amino acid abbreviation is used with the residue number given in superscript (i.e. Xaan)

TABLE 1

| Amino Acid | Three-letter Abbreviation | One letter Abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Figure 1:
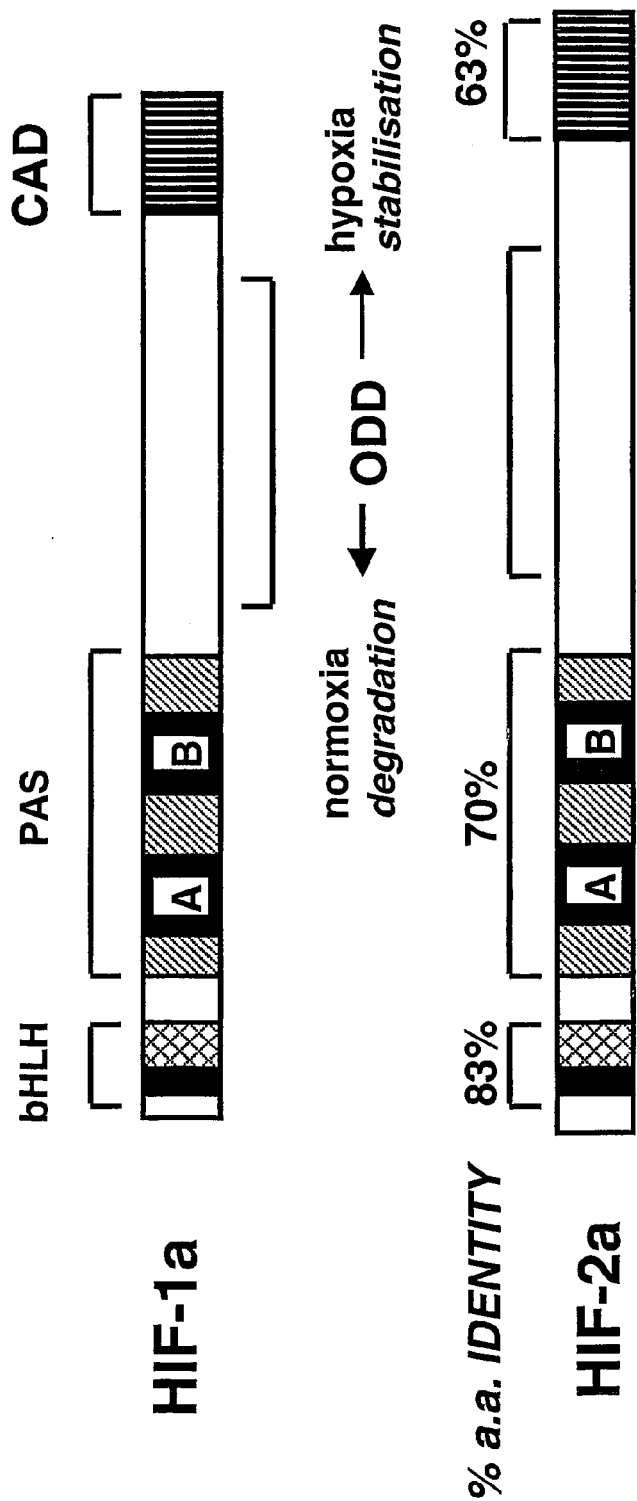
FIG. 1. Is an illustration of the overall structure of the HIF-1α and HIF-2α protein showing the location of the domains present on a linear amino acid map, and also showing amino acid homologies between the two HIF proteins for certain of the domains. bHLH refers to the basic Helix-Loop Helix; PAS refers to the Per-Arnt-Sim homology region; CAD, refers to C-Terminal transactivation domain and ODD refers to oxygen dependent degradation domain.
Figure 2:
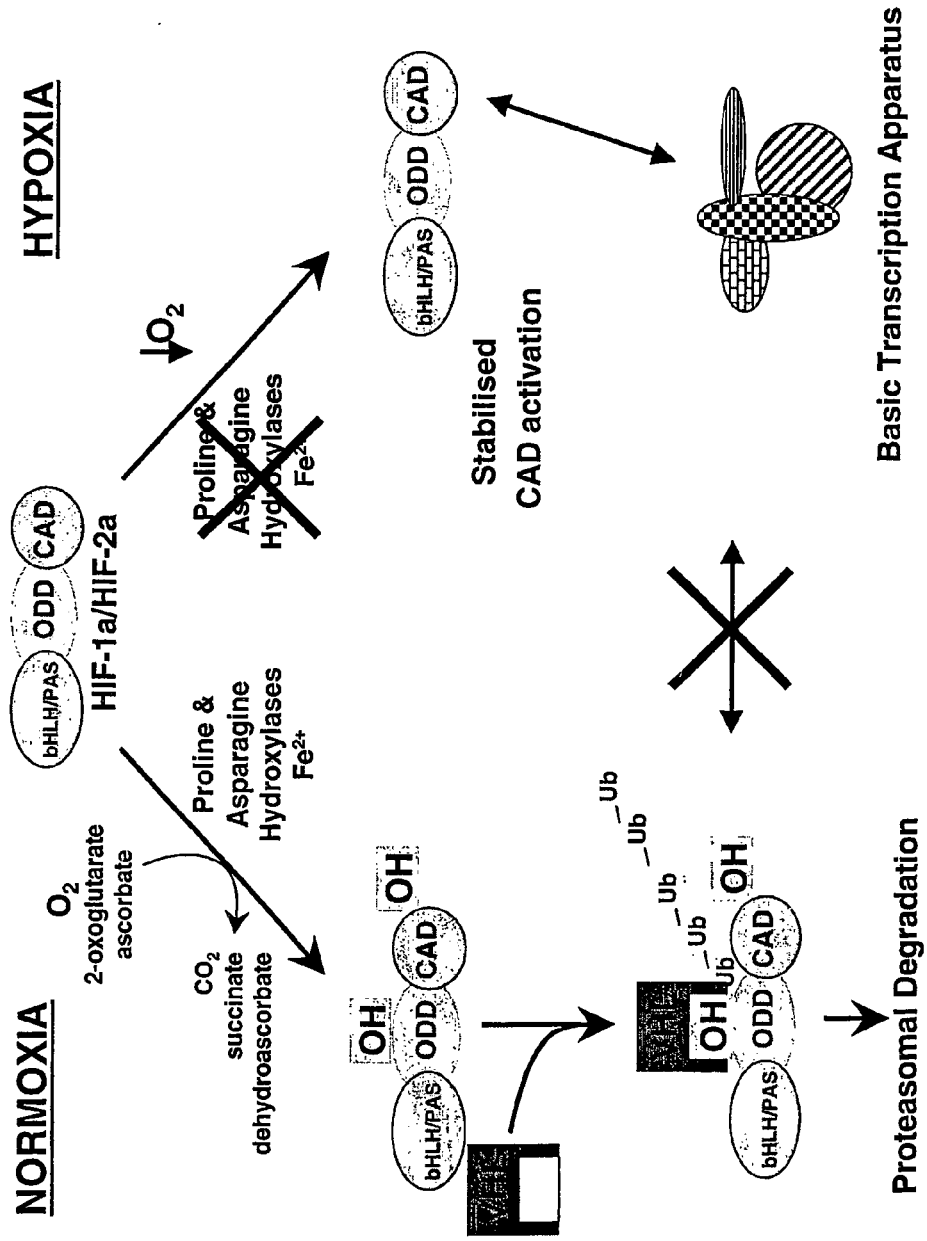
FIG. 2. Is an illustration of the oxygen dependent mechanism in place to regulate the turnover and CAD activity of the HIF-1α and HIF-2α proteins. bHLH refers to the basic Helix-Loop Helix; PAS refers to the Per-Arnt-Sim homology region; CAD, refers to C-Terminal transactivation domain; ODD refers to oxygen dependent degradation domain and VHL refers to the von-Hippel-Lindau factor.

HIF (Hypoxia Inducible Factors) proteins have been the subject of some scientific research. Two basic forms have been described the first described form is known as HIF-1α which is the subject of U.S. Pat. Nos. 5882914 and 6222018 in the name of Semenza. The second basic form is known as HIF-2α, also known in the scientific literature as EPAS (Endothelial PAS protein) MOP2, HIF-like factor (HLF) and HIF-related factor (HRF). These have been described above in some detail with reference to FIG. 1. The organisation of functional domains of both of these HIF proteins is as follows. An arrangement toward the N terminus of bHLH/PAS domains which are important for dimerisation and DNA binding, Oxygen Dependent Degradation Domains (ODDs) which mediate protein turnover; and C-terminal transactivation domains (CAD) which are important for inducing transactivation of transcription of target genes. Modification of the CAD domain as envisaged by the first two aspects of the invention to make the domain resistant to asparagine hydroxylation and therefore constitutively active may be applicable to HIF-1α and HIF-2α, or indeed other HIP that may be found in due course that have a homologous CAD domain. A third HIP is known namely HIF-3α however this is not pertinent to the present invention because this does not have a CAD domain.

It will be understood that the invention is applicable to variants of the HIF proteins where variations occur outside of the CAD domain. Thus deletions of the protein, for example, deletion of all or part of ODD may be preferred in that this domain enhances protein turnover which turnover is mediated by a prolyl hydroxylase, and it may be desired to maintain function of the protein at hypoxia and normoxia. The entire ODD may be deleted to achieve this, thus providing a truncated HIF protein having dimerisation and DNA binding domains as well as CAD domain. Alternatively the proline subject of hydroxylation may simply be substituted so that ubiquitination cannot be achieved. Additionally other modification may be made to the HIF protein. Thus for example it is known that simple amino acid substitutions do not materially affect the function of the protein. In particular, conservative amino acid substitutions might be made.

One or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly conservative amino acid substitutions are:
  (a) Lys for Arg or vice versa such that a positive charge may be maintained;
  (b) Glu for Asp or vice versa such that a negative charge may be maintained;
  (c) Ser for Thr or vice versa such that a free OH can be maintained;
  (d) Gln for Asn or vice versa such that a free NH2 can be maintained;
  (e) Ile for Leu or for Val or vice versa as roughly equivalent hydrophobic amino acids; and
  (f) Phe for Tyr or vice versa as roughly equivalent aromatic amino acids.

However it will be understood that less conservative substitutions may still be made without affecting the activity of the CAD or CAD derived agent.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting CAD or CAD derived agent. The invention may also contemplate changes that enhance these activities.

The essential alteration contemplated for HIF proteins inhibit hydroxylation of the asparagine and is preferably within the asparagine hydroxylation motif. The inhibition may be complete so that, for example, no hydroxylation occurs on the asparagine. Where for example the asparagine residue is substituted for another amino acid then it is anticipated that no hydroxylation of that amino acid will occur. It is anticipated that other substitutions of amino acids will also provide for inhibition of asparagine hydroxylase. The inhibition may not be complete so that a proportion of the HIF proteins will be hydroxylated but the remainder will give a significant transactivation function. It is thought that the present regulatory system is one where a hydroxylase is active, and accordingly the proportion of HIF proteins that are hydroxylated at the asparagine residue will result from a balance between the rate of formation of the HIF protein, the rate of hydroxylation by the asparagine hydroxylase, and the rate of turnover of the HIF protein, this therefore results in a dynamic pool of HIF protein a proportion of which will be hydroxylated and a proportion of which will not. With a normal CAD domain at normoxia the proportion of HIF proteins hydroxylated in the CAD domain will be quite high, inhibition of the hydroxylation by the asparagine hydroxylase will decrease that level. The degree of inhibition of hydroxylation need not be complete but adequate to provide an appreciable increase in the proportion of the pool of HIF proteins that are not hydroxylated and therefore results in an increase in the capacity of the pool of HIF to give its transactivation effect under normoxic or hypoxic conditions.

As indicated above the alteration might for a HIF protein be either in the asparagine hydroxylase binding motif or in the asparagine hydroxylase hydroxylation motif. For simplicity reference will now be made to amino acid sequence of what is thought to be approximately the total extent of the CAD domain of the two known HIF proteins HIF-1α and HIF-2α.

agine also effects an approximately 50% decrease in hydroxylation. Thus the hydroxylation motif might be considered to be TSYDCEVNAPIQGSRNL [SEQ ID NO. 4] for human HIF 1α, and TRYDCEVNVPVPGSSTL [SEQ ID NO. 5] for mouse HIF 2α.

Figure 8:
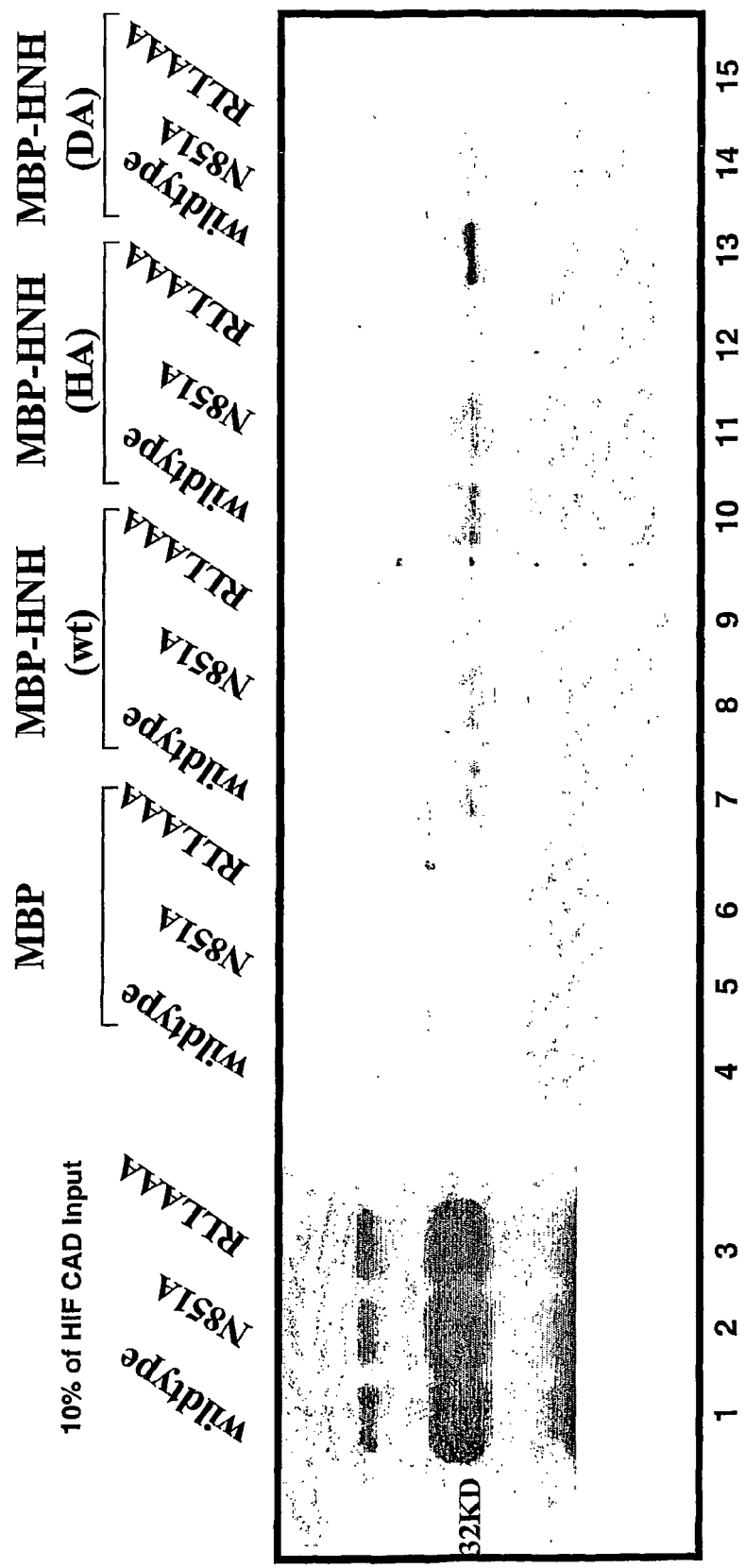
FIG. 8. Interaction between the HIF CAD and the HNH asparagine hydroxylase is dependent upon the RLL motif. The CAD containing C-terminal 100 amino acids of HIF-2a was in vitro translated in the presence of $^{35}S$-methionine. Wild type and mutant CADs (N851A point mutant and RLL to AAA triple mutant) were translated and incubated with amylose-agarose resin prebound with recombinant MBP fusion proteins containing either wild type HNH or mutant HNH sequences (HA and DA, which lack hydroxylase activity). The resin mixtures were washed before the pulled down proteins were analysed by SDS-PAGE and autoradiography. Lanes 1-3 show 10% of the input translation mixtures. Lanes 4-6 show lack of CAD interaction with the MBP portion of the MBP-HNH fusion proteins. Lanes 7-15 show that CAD-HNH interaction depends on the RLL motif but not the Asn851 target of hydroxylation nor the catalytic activity of the HNH enzyme.
Figure 9A:
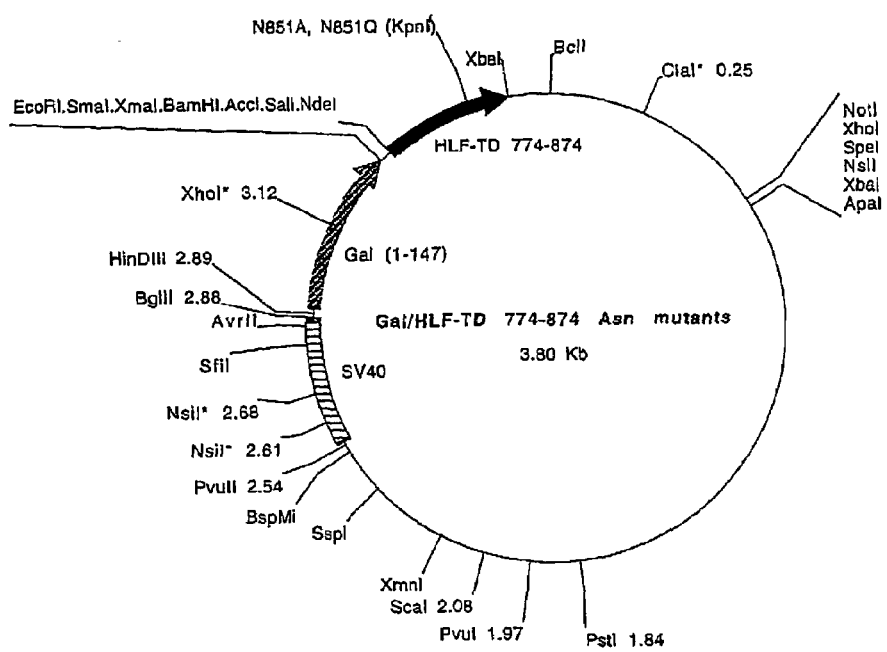
FIG. 9. Are diagrams showing vectors carrying altered HIF1 proteins or portions thereof. A) represents two different plasmids carrying respectively amino acid substitutions in HIF 2α 774-874 made in HIF/pBSK using quick change. Mutants were digested with SALI/DraI and cloned along with NdeI/SalI gragment from Gal/HLF-TD774-874 in a three way ligation into Gal0 digested NdeI/XbaI vector. This is thus a vector encoding a chimeric protein. Note the unique KpnI site. B) represents two different plasmids carrying respectively amino acid substitutions in HIF 1α 727-826 made in Gem 7 SL using quick-change. The amino acid substitutions are N803A and N803Q. Mutants were digested with SaII/XbaI and cloned into SaII/XbaI digested GalO. This is thus a vector encoding a chimeric protein. Unique restriction site NarI was introduced by silent mutation. C) represesents the complete HIF-1α cloned into pefbox-cs. The HIF-1α has had an N803A amino acid substitution. D) represents a vector with HIF 2α fragement 774-874 incorporating BamHi, myc and NdeI sites), digested PCR product with BAMh1/NotI digested EF.HIF-TD 727-826.puro 6.
Figure 9B:
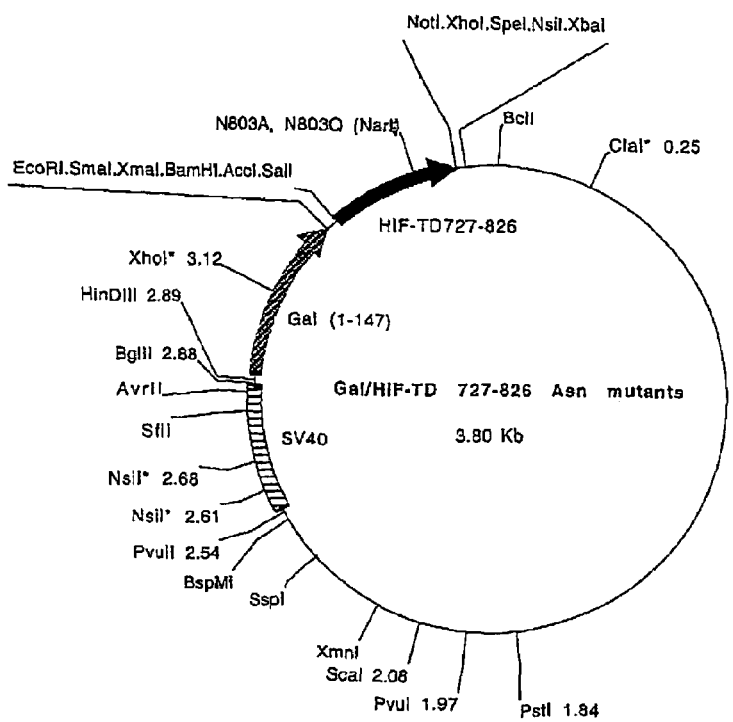
Figure 9C:
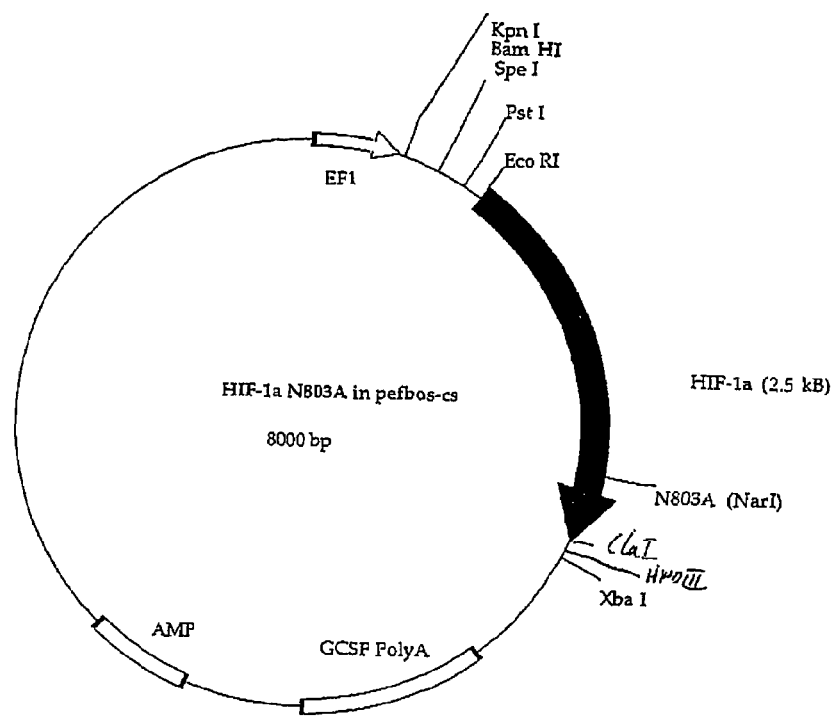
Figure 9D:
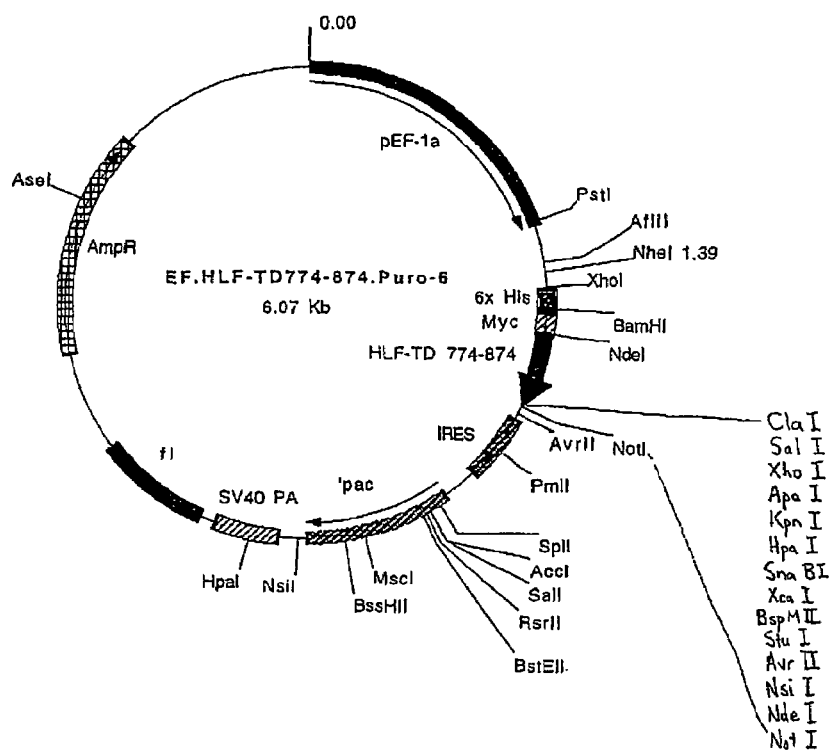

Likewise it has been found (O'Rourke et al., 1999) in substituting amino acids that the transactivational activity of the CAD domain is made constitutive by the substitution of the amino acids RLL. It is postulated that these amino acids are also critical for the hydroxylation of the target asparagine. Association experiments confirm that binding between HIF and asparagine hydroxylase FIH does require RLL because amino acid substitutions interfere with that binding (FIG. 8). It is considered most probable that these amino acids are part of a binding motif for the asparagine hydroxylase, and that amino acids adjacent to RLL are also likely to be part of that binding sequence. The extent of the putative binding sequence are indicated above with underline amino acid sequence with the designation "binding motif". It is proposed therefore that one or more conservative substitutions within the asparagine hydroxylase binding motif may give rise to an altered HIF which has lowered hydroxylation of the target asparagine by the asparagine hydroxylase. Thus the asparagine hydroxylase binding motif might be considered to be ACRLLGQS [SEQ ID NO. 6] for human HIF-1α, and ASRLLGPS [SEQ ID NO. 7] for mouse HIF-2α.

There may well also be other parts of the CAD domain whereby amino acid substitutions, or other alterations can be

```
humanHIF-1α 776-SDLACRLLGQSMDESGLPQLTSYDCEVNAPIQGSRNLLQGEELLRALDQVN826   [SEQ ID NO. 2]

mouseHIF-2α 824-SGVASRLLGPSFEPYLLPELTRYDCEVNVPVPGSSTLLQGRDLLRALDQAT-874   [SEQ ID NO. 3]

Binding motif          hydroxylation motif
```

Figure 7:
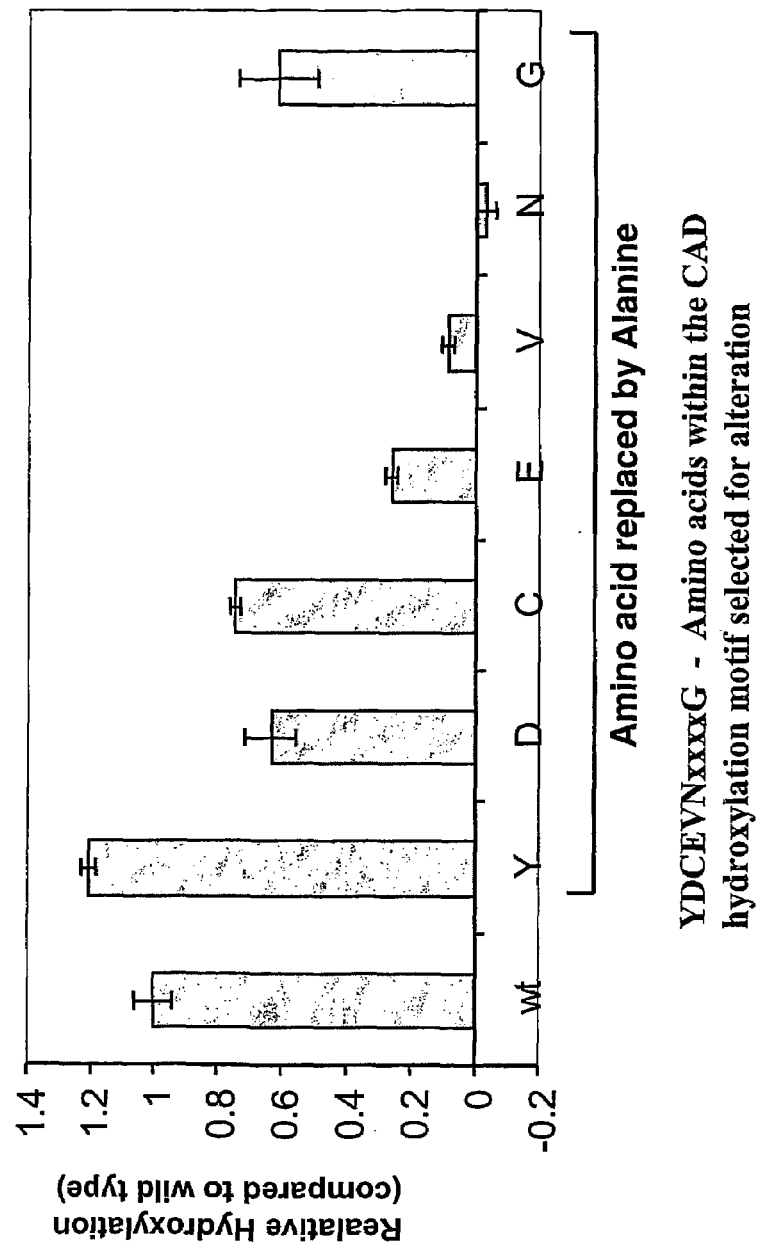
FIG. 7. Importance of selected amino acids within the HIF CAD asparagine hydroxylation motif. Recombinant HIF-1α CAD, either wild type or point mutant where alanine has replaced the indicated amino acid, was incubated with purified, recombinant HNH in a reaction cocktail containing $FeSO_4$, ascorbate and [$^{14}C$]-2-oxoglutarate. Hydroxylation was assessed by counting liberated $^{14}CO_2$ and the data shown represents the degree of hydroxylation for each mutant normalised to the level observed for the wild type HIF-1α CAD sequence.

It has been shown by the present inventors that under normal oxygen levels the asparagine at residue 803 of human HIF-1α and the asparagine residue at 851 of mouse HIF-2α are hydroxylated in which case the transactivational domain has very low activity. If either of these two asparagines is conservatively substituted, for example, for an alanine then the CAD domain still exhibits its transactivational properties but the target asparagine is not hydroxylated. It can be seen however that adjacent the target asparagine residue of the CAD domain are very conserved amino acid sequences, these are underlined above and designated as hydroxylation motif indicating that this sequence could be considered to be an amino acid motif that is required for the asparagine hydroxylase to catalyse the hydroxylation of the target asparagine. It is postulated that substitution of these amino acids will also interfere with the hydroxylation of the target asparagine in vivo, and that should some or all of these be substituted conservatively then the transactivational activity of the CAD domain may be kept intact. Within this motif, the valine (V) immediately preceding the target asparagine seems particularly important, as altering this valine to alanine results in very low levels of hydroxylation in an in vitro hydroxylation assay (FIG. 7). Alteration of other amino acids close to the asparagine have varying effects on the ability of the FIH-1 asparagine hydroxylase to modify the target asparagine in vitro. Substituting alanine in place of tyrosine (Y) has little effect, whereas individually replacing D, or C residues for alanine effects an up to 50% decrease in hydroxylation of the target aspargine. The glutamic acid (E) residue is more important or efficient hydroxylation than D or C. Alteration of the conserved (G) 5 amino acids C-terminal to the target asparmade that inhibit hydroxylation of the target asparagine. Thus for example deletion of the initial portion of the CAD domain up to about amino acid 786 in HIF-1α may still give rise to its transactivational characteristic but prevent hydroxylation of the target asparagine by preventing the binding of the asparagine hydroxylase to the CAD domain. Constitutive activity is found with such deletion in chimeric constructs (Ratcliffe et al., 1998). It is anticipated that a similar finding is likely for HIF-2α with constitutive expression occurring up to about amino acid 841.

This invention may additionally contemplate the use of an altered HIF CAD domain in a context other than for HIF functions. Specifically contemplated are alterations in the CAD domain in particular in the asparagine hydroxylation motif or other amino acids proximal the C terminus in relation to the asparagine hydroxylase binding motif. Such altered HIF CAD domain which may also have further alterations of amino acids that do not impact on the capacity of the HIF CAD domain to act as a substrate for the asparagine hydroxylase or to act as a transactivator, as contemplated above (as applicable) for the HIF protein such as for example by conservative amino acid substitutions. The second aspect contemplates chimeric proteins whereby the HIF CAD domain is adjacent a DNA binding domain other than that of HIF. This might therefore be useful in providing for a novel transcriptional enhancing molecule. Such binding proteins might be any that fall into the common classes of DNA binding domains such as basic Helix-Loop-Helix, Zinc Finger, Homeodomain, Helix-Turn-Helix.

These proteins with altered HIF CAD properties might be administered to a patient and perhaps a particular site in the patient requiring better adaptation to a hypoxic micro environment.

Another aspect of the present invention encompasses nucleic acids encoding any of the altered protein or chimeras. Typically the nucleic acid will take the form of DNA, however the nucleic acid might take the form of RNA. The nucleic acid may be expressed in a vector which may be suitable for therapeutic application. The vectors may be any one of the many available simply for replication and production of the altered protein in vitro. However the vector might be chosen from the type intended to introduce the nucleic acid into a patient. Possible vectors are naked DNA containing broad spectrum mammalian promoters such as β actin or elongation factor, or common gene therapy vectors such as those derived from adenovirus, adeno-associated virus or lentivirus.

It might thus be desired to provide for expression of the protein with altered HIF CAD domain in a particular tissue. DNA may be administered in linear or other naked form for a relatively short term effect, but probably more desirably it may be administered by transfection such as, for example where the nucleic acid is incorporated into a retroviral vector suitable for human or animal use. In an alternative form the nucleic acid encoding the altered protein may be transformed into a cell. The cell may be a mammalian cell and perhaps a precursor cell line such as for example an ES cell or other precursor cell capable of differentiating in the target tissue of a patient, preferably of course such a cell might be a stem cell capable of differentiating and self replicating. These cells might be introduced into the patient in the target tissue to provide for long terms expression to promote vascularisation.

An asparagine hydroxylase capable of binding HIF-1a and HIF-2a (termed HNH for HIF N(letter code for asparagine) Hydroxylase) has now been identified (Lando et al., 2002). This asparagine hydroxylase was earlier shown to repress HIF-1 transcriptional activity and has also been termed FIH-1 (Mahon et al., October, 2002), although this report did not describe any hydroxylase function for FIH-1. We were the first to describe a hydroxylase function for FIH-1 (Lando et al., 2002)It is anticipated that asparagine hydroxylase activity will be found in cell extracts from cells that have been grown in normoxic conditions. The present invention for the first time has identified the existence of such an hydroxylase, that is not to say that this will be the only asparagine hydroxylase ever isolated, other do exist. An aspartyl/asparagine hydroxylase has previously been described as an oxygen and $Fe^{2+}$ dependent enzyme that hydroxylates residues in EGF (Epidermal Growth Factor) like domains of various proteins (Dinchuck et al., 2000). EGF like domains do not exist in the CADs, therefore FIH-1 and further novel asparagine hydroxylases may exist to modify HIF-1α and HIF-2α.

The asparagine hydroxylase of the present invention will act on HIF-1α and 2α in normoxic conditions and may act on other proteins with similar binding and hydroxylation motifs to those described above. The present invention also provides for a method of isolating asparagine hydroxylase enzymes, by reason of its affinity for the CAD domain or portions thereof. The method may contemplate the immobilisation of the CAD domain or portion thereof, contacting the immobilised CAD domain or portion thereof with a cell extract, washing off the cell extract under mild condition, followed by washing off with more stringent conditions. The cell extract may be fractionated before contacting the immobilised CAD domain or portion thereof by any one of the many fractionation techniques known in protein purification protocols, such as ammonium sulphate fractionation or size fractionation by chromatographic methods. The use of a fractionated cell extract may assist with the purification. An alternative method is to immobilise a cell extract or fractionated or partially purified cell extract, by for example electrophoresing on a gel or other separation method, and then applying labelled CAD domain or preferably a portion thereof to identify the concentrated band. Such bands can be cut from the gel and purified. Intracellular screens to discover a cDNA that encodes the interacting hydroxylase would include yeast or mammalian two hybrid assays.

Another general approach is to undertake a bioinformatic analysis to derive likely genes that encode the enzyme. This is undertaken by the use of suitable databases of protein to look for enzymes that show sequences common to for example hydroxylases, and more specifically asparagine hydroxylases. The candidates are either cloned or obtained and purified or semi purified protein is tested by in vitro hydroxylation assays, binding assays or reporter gene assays in cells in methods similar to those that provided the data shown in the FIGS. 7, 8 and 3.

In the above it may be desired to use the affinity of an entire HIF CAD domain, however certain regions are not required for the asparagine hydroxylase binding and may have affinity for other matter in the cell extract or fractionated cell extract, leading to difficulties with the purification. Accordingly cut down versions of the HIF CAD that encompass the asparagine hydroxylase binding motif or the binding motif and hydroxylation motif may be used. Particularly desirable is where these two motifs are maintained in the same relative position as is found in the HIF CAD domain. It is preferred that the CAD domain or portion thereof is in the unhydroxylated form because that more specifically resembles the substrate of the asparagine hydroxylase that is sought to be purified.

Whilst reference has been made above to the purification of the asparagine hydroxylase and it is thought unlikely that a counterbalancing enzyme exists there may well be an asparagine dehydroxylase. The present invention therefore encompasses a method of isolating an asparagine dehydroxylase for dehydroxylating the target asparagine. The CAD domain or portion therefore may be used in similar manner as for the isolating the asparagine hydroxylase, except that the cell extract is made from cells grown under hypoxic conditions and perhaps the method of purification is all carried out under hypoxic condition. The CAD domain or portion therefore also preferably has the target asparagine in the hydroxylated form.

The above methods also provide a basis for the isolation of antagonists of the asparagine hydroxylase. Thus small molecules can be tested for their capacity to bind to the CAD domain and more particularly to the asparagine hydroxylase binding motif or the asparagine hydroxylase hydroxylation motif by affinity methods. Candidates that exhibit affinity may be used for therapeutic purposes similar to those for with the altered protein of the first and second aspects of the invention might be used for.

The fourth aspect of the invention encompasses a method of screening for agonists as well as antagonists, including providing a preparation containaing asparagine hydroxylase and a HIF CAD domain or portion therof and adding a candidate agonist or antagonist, and measuring inhibition or enhancement of hydroxylation of the target asparagine.

The HIF CAD domain or portion thereof may be any form to which the asparagine hydroxylase can bind and various suitable forms are discussed above, and are where the target asparagine is in an unhydroxylated state. Preferable the HIF CAD domain or portion thereof is immobilised, for example in a multiwell tray. The preparation containing the asparagine hydroxylase might simply be a crude cell extract, including or excluding cell wall or cell membrane, or the preparation may be fractionated crude cell extract, various methods of fractionating the cell extract may be used and an appropriate fraction identified as having the majority of activity can be used in the preparation. Preparations of crude or purified recombinant asparagine hydroxylases may also be used. The candidate agonist or antagonist might be any molecule that might potentially be used for therapeutic purposes, including polysaccharides, peptides, nucleic acids, or other organic compounds a variety of which may be manufactured by known combinatorial approaches to screening. The preparation containing asparagine hydroxylase and the candidate agonist or antagonist are added to the immobilised HIF CAD domain or portion thereof, after a suitable incubation time, the non-immobilised material is washed off, and the HIF CAD domain or portion thereof is probed for hydroxylation of the target asparagine. The probing might be by mass spectrometry of a peptidic fragment of the HIF CAD domain or portion thereof, alternatively carbon dioxide capture assay that measures aspartyl-b-hydroxylase activity may be employed (Analytical Biochem., vol.271, pp137-142 (1999)

The present invention might also encompass purified HIF-1α and/or HIF-2α or fragments thereof having the target asparagine in an unhydroxylated form.

Methods

Reporter Gene Assays

Human embryonic kidney 293T and rat pheochromocytoma PC12 cells were maintained in Dulbecco's Modified Eagles Medium (DMEM) supplemented with 10% foetal calf serum. For transient transfections, cells were plated onto 24 well plates at a density of $2.0 \times 10^4$ cells/well. After 24 hrs, transfections were carried out using LipofectAMINE 2000 (GibcoBRL) according to the manufacturer's instructions. Each transfection contained 300 ng/well of G5E1-luc reporter plasmid, 10 ng/well Renilla-Luc internal luciferase control (Promega) and 100 ng/well of each GalDBD fusion plasmid as specified. Following 6 hrs of transfection, cells were either maintained at 20% $O_2$ (normoxia) or treated as specified. After 16 hrs treatment, cells were harvested, lysed and extracts analysed using the Dual Luciferase Reporter Assay Kit as outlined by the manufacturer (Promega).

Detection of Proteins by western Blotting

Isolated cell pellets were lysed in whole cell extract (WCE) buffer (10 mM Tris pH7.9, 0.42M $NaCl_2$, 0.5% NP40, 25% Glycerol, 0.2 mM EDTA, 1.5 mM $MgCl_2$, 1 mM DTT, protease inhibitors) for 10 min at 4° C. Lysed extracts were then clarified by centrifugation at 12,000 g for 15 min. The protein concentration of clarified lysates was determined using the Bradford assay (Biorad). Protein samples were then resolved on 12.5% Tris-Tricine gels. For the HIF-2α774-874 stable line, 10 μg of WCE was analysed by immunoblotting with the anti-myc 9E10 monoclonal antibody. For detection of GalDBD/HIF-1α727-826 and GalDBD/HIF-2α774-874, 293T cells were transfected with the relevant expression plasmid and WCE were separated by SDS-PAGE before immunoblotting with antibodies raised against the C-terminus of HIF-1α or HIF-2α, respectively.

Hypoxia Treatment

Normoxic (20% $O_2$) cells were cultured under a humidified atmosphere of 5% $CO_2$/95% air. For exposure to hypoxia (<1% $O_2$) cells were placed inside an air tight chamber along with an AnaeroGen sachet (OXOID) according to the manufacturer's instructions.

HIF-2α CAD Purification

Samples for MS analysis were isolated from a 293T stable cell line that expressed HIF-2α774-874. After normoxic culture or treatment with hypoxia or DP as specified, cells were washed once with PBS, then lysed with binding buffer (100 mM Na-Phosphate pH8.0, 8M Urea, 0.1% NP40, 0.15M $NaCl_2$, 5 mM imidazole, 1 mM βMe, 0.05 mM $Na_3VO_4$, 0.1 mM NaF, 0.5 mM β-Glycerophosphate, protease inhibitors). Clarified lysate was then loaded onto a column containing Ni-IDA agarose (Scientifix, Australia) equilibrated in binding buffer. After extensive washing with wash buffer (100 mM Na-Phosphate pH8.0, 8M Urea, 0.5M $NaCl_2$, 20 mM imidazole), bound proteins were eluted from the column with Elution buffer (100 mM Na-Phosphate pH8.0, 8M Urea, 200 mM imidazole). Protein sample eluted from the Ni column was then loaded onto a Butyl C4 HPLC column (Brownlee, PerkinElmer) that had been equilibrated in 0.1% trifluoroacetic acid (TFA). HIF-2α774-874 was then subsequently eluted with increasing gradient of 80% acetonitrile, 0.1% TFA. Purified HIF-2α774-874 was then subjected to MS analysis.

An Anaerobic Workstation III (Don Whitley Scientific, UK) was used to prepare hypoxic HIF-2α774-874 protein for MS analysis. For hypoxic preparation, cells were washed and lysed inside the anaerobic workstation with buffers that had been deoxygenated overnight. After cell lysis the purification was carried out at ambient $O_2$ conditions.

Methods for Analysis of Post-Translational Modifications

Preparation of Samples for Mass Spectrometry

HPLC fractions, consisting of aqueous acetonitrile with 0.1% (v/v) trifluoroacetic acid, were reduced in volume to 50-100 μl and 10 μl of 1M $NH_4HCO_3$ were added to raise the pH to approximately 8. Dithiothreiotol was added to a final concentration of 2 mM and the solutions were incubated for 20 min at 37° C. prior to adding iodoacetamide to a final concentration of 20 mM and allowing alkylation to proceed for a further 30 min at 37° C. in the dark. Trypsin digestion was achieved by adding 1 μg of sequencing grade modified trypsin (Boehringer) directly to the unfractionated reduction and alkylation mixture and incubation for 4 h at 37° C. Tryptic digests were subsequently acidified by adding 50 μl of 1% (v/v) formic acid and the contents aspirated through C18 ZipTips (Millipore) that had been prewetted with 100% methanol and washed with 5% (v/v) aqueous methanol containing 0.1% (v/v) formic acid using a 20 μl pipettor. The ZipTips were washed twice with 20 μl of 5% (v/v) aqueous methanol containing 0.1% (v/v) formic acid and the washes combined with the initial aspirates and retained for later processing, if required. Adsorbed peptides were eluted from the ZipTips with 10 μl of 70% (v/v) aqueous methanol containing 0.1% (v/v) formic acid. All incubation steps were performed with constant shaking.

Theoretical products of tryptic digestion were generated using the Bioanalyst component of Analyst QS software (Applied Biosystems).

Matrix-Assisted Laser Desorption/Ionization—Time of Flight Mass Spectrometry (MALDI-TOF-MS)

Tryptic digests were analyzed using a Bruker Reflex MALDI-TOF-MS operated in the positive ion reflector mode. MALDI-TOF-MS data were acquired and analyzed using the Bruker XMass suite of software (Lopaticki et al., 1998; Pitt et al., 2000; Gorman et al., 1997). 2,6-dihydroxyacetophenone (DHAP—Fluka)/diammonium hydrogen citrate (DAHC—Fluka) matrix was prepared as described previously (Gorman et al., 1996). Samples (1-2 μl) were mixed with an equivalent volume of matrix, 1 µl of the mixtures were deposited on a Bruker Scout 26 MALDI target and allowed to air dry for 10 min before analysis.

Post-source decay (PSD) analysis was performed using the Bruker Reflex mass spectrometer and samples prepared in cyano-4-hydroxycinnamic acid as the matrix essentially as described previously (Gorman et al., 1997; Lopaticki et al., 1998). Variation to the previously described procedures involved use of a 100 ns delay before extraction of ions from the source, and data acquisition using a 1 GHz digitizer.

Tandem Mass Spectrometry (MSIMS)

Peptides were subjected to partial sequence analysis by tandem mass spectrometry (MS/MS) in the positive ion mode using a Sciex QSTAR-Pulsar Quadrupole-quadrupole (Qq)—TOF-MS under the control of Analyst QS software. Tryptic digests were sprayed from 60% (v/v) aqueous methanol containing 0.1% (v/v) formic acid. Approximately 2 µl of diluted digests were loaded into drawn capillaries coated with gold/palladium (Protana NanoES capillaries) and fitted onto a Protana NanoES electrospray ion source. Ions were sprayed with a potential of 850 V on the sample capillary. Collisionally-activated decomposition of peptides was achieved by selecting doubly charged ions of interest using Q1 at low resolution and manually varying the collision energy to achieve optimal spread of fragments across the desired TOF mass ranges and using nitrogen as the collision gas.

Identification of proteins was achieved by using MS/MS spectra to search the Mascot database (www.matrixscience.com) with mass error constraints of 0.1 Da and 0.05 Da for parent ions and fragments ions, respectively.

Expression of Tile Asparagine Hydroxylase FIH-1

FIH-1 was expressed in bacteria as a fusion protein with the maltose binding protein for rapid purification. Bacteria (BL21-CodonPlus-RIL *E-coli* strain from Stratagene) containing a standard IPTG inducible MBP/FIH-1 expression vector were grown at 37° C. to A600=0.8 then induced with 200 uM IPTG and shaken for 6 hours 30° C. Soluble protein was purified using amylose-agarose resin and eluting with 10 mM maltose according to standard procedures.

Pulldown Assays

The C-terminal 100 amino acids of mouse HIF-2a (ie 775-874), either wild type or the mutants N851A, or RLL to AAA, were in vitro translated in the presence of $^{35}$S-methionine from pET32 vectors using the Promega TNT translation system as recommended by the manufacturers. The HIF CAD fragments also have an N-terminal thioredoxin/6-histidine tag supplied by the pET32 vector.

Crude bacterial lysates containing recominant MBP (Maltose Binding Protein, alone for a negative control) or recombinant chimeric proteins containing MBP fused to either wild type HIF Asparagine Hydroxylase (HNH), or mutant HNH proteins which lack hydroxylase activity (ie H199A and D201A, which are noncatalytic mutants) were bound to amylose-agarose resin and washed, but not eluted. 25 ul of resin (bound to approx 100 ng of MBP-HNH) was shaken 2 hrs (4° C.) with 10 ul of the HIF-2a translation reaction and 165 ul of binding buffer (150 mM NaCl, 20 mM Tris(pH 8.0), 0.5 mM EDTA, 0.5% NP40). Samples were centrifuged 1500 rpm, 30 secs (room temp) to pellet resin, and the supernatant discarded. Resin was then washed three times with 1 ml of the binding buffer. Pulled-down HIF-2a (775-874) was then eluted from the MBP-HNH resin by boiling for 5 mins with 2×SDS sample buffer (40 ul). After centrifuging 30 secs/1500 rpm, 30 ul of the supernatant was separated by electrophoresis through a 12.5 % polyacrylamide gel. The gel was dried and exposed to autoradiography.

Hydroxylation Assays

A method to measure the extent of hydroxylation was adapted from a published $^{14}CO_2$ capture assay (Zhang et al., 1999). The recombinant C-terminal 90 amino acids of human HIF-1a (150 uM), either wild type or point mutant where alanine replaced the indicated amino acid, was incubated with purified, recombinant HNH (200 nM) in the presence of $FeSO_4$ (1.5 mM) and ascorbate (4 mM) in an ice cold buffer containing 40 mM Tris (pH 7.0), DTT (0.5 mM) and NaCl (150 mM). [$^{14}$C]-2-oxoglutarate (40 uM) was then added and immediately a filter soaked in saturated $Ca(OH)_2$ was suspended above the reaction and the reaction tube sealed. Following incubation for 60 min at 37° C., the filter was removed, dried and soaked in 120 ul of Hi-Safe Scintillation fluid before being placed in the dark for 15 min. prior to scintillation counting.

Results

Figure 3:
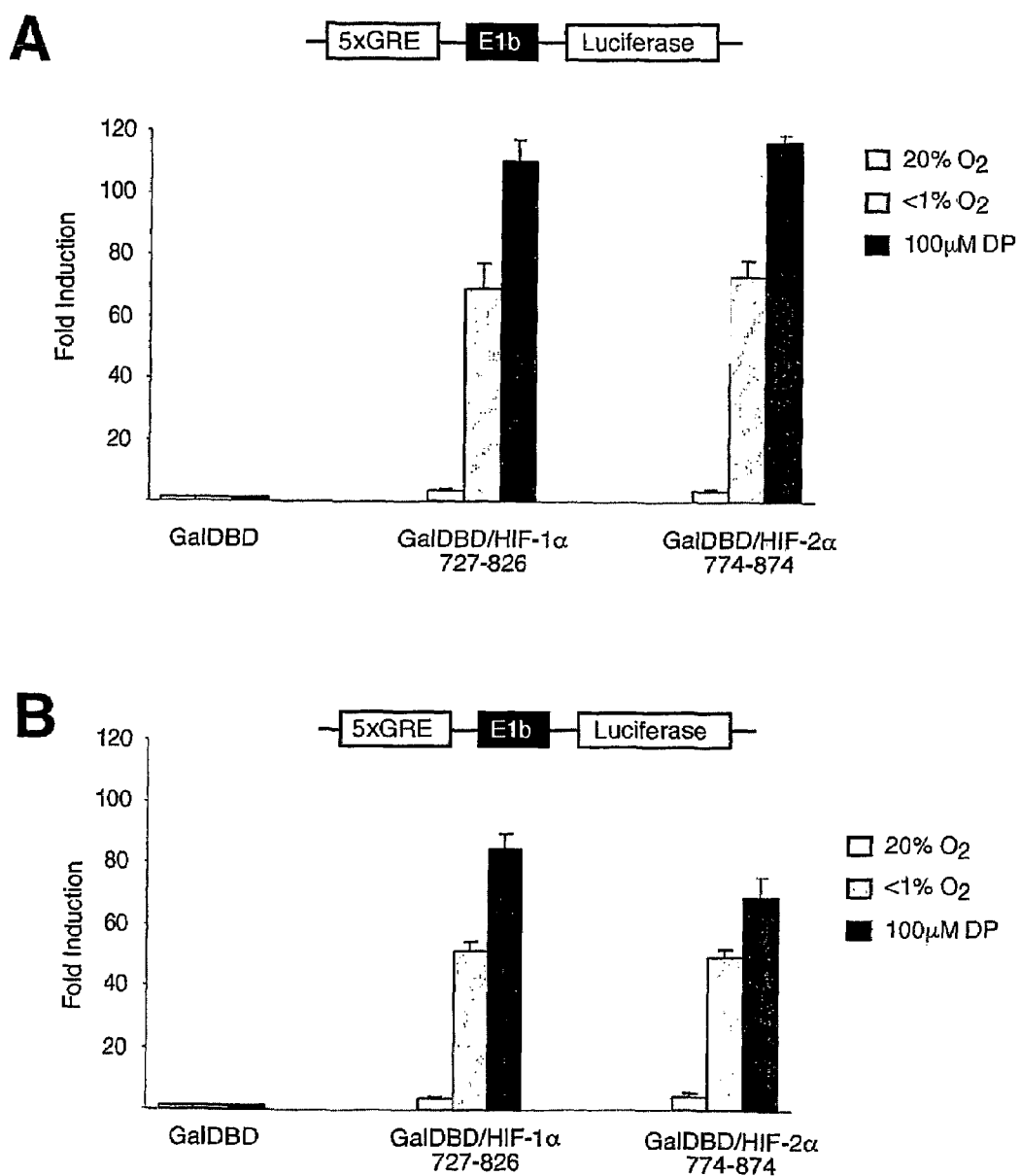
FIG. 3. Expression vectors for either the Gal4 DNA Binding Domain or the indicated GalDBD HIF-1α and HIF-2α CAD chimeric proteins were contransfected with a Gal4 response element containing luciferase reporter gene and an internal control renilla luciferase reporter gene. Transfected HEK293T (A) or PC12 (B) cells were left untreated, or subjected to hypoxia or 2,2'-Dipyridyl (DP) treatment for 16 h, before luciferase activities were measured by the dual luciferase assay (Promega). Data are the average of three transfections±standard deviation.

Hydoxylation of an Asparagine Residue in the C-terminus of Hypoxia Inducible Factors has a Critical Influence on Protein Function The Hypoxia Inducible Factor HIF-1α is a ubiquitous bHLH/PAS (basic Helix-Loop-Helix/Per Arnt-Sim homology) transcription factor which plays a key role during adaption to low oxygen stress. Target genes for HIF-1α include those of erythropoietin (EPO), vascular endothelial growth factor (VEGF) and a host of genes encoding glycolytic enzymes involved in anaerobic energy production (Semenza, 2000). Disruption of the HIF-1α gene in mice has established that it is essential for vascularisation of the embryo (Iyer et al., 1997, Ryan et al., 1998), while a host of studies implicate roles for HIF-1α in tumour angiogenesis and the pathophysiology of ischemic disease (Semenza, 2000). A second, highly related hypoxia inducible factor, variously termed endothelial PAS protein (EPAS Semenza, 2000, Tian et al., 1997), HIF-Like-Factor (HLF, Ema et al., 1997) or HIF-2α, is also essential during mouse development (Tian et al, 1998; Peng et al., 2000), although its exact function is not understood. Two separate domains within these proteins are known acceptors of hypoxia signalling pathways. The first is the oxygen dependent degradation domain (ODD) which, at normoxia, is subject to posttranslational modification by an oxygen, Fe(II) and 2-oxoglutarate dependent prolyl hydroxylase (Ivan et al., 2001; Jaakkola et al., 2001). The hydroxylated proline confers interaction with the von Hippel-Lindau ubiquitin ligase complex, resulting in ubiquitination and rapid proteolysis of the HIF proteins by the proteasome. During hypoxia, the prolyl hydroxylase ceases to function and the proteins escape surveillance of the ubiquitin-proteasome pathway, resulting in a dramatic increase of their half lives. A second region which senses hypoxia lies within the C-terminal 100 amino acids of HIF-1α and HIF-2α, which functions as hypoxia inducible transactivation domain (termed the CAD, C-terminal Activation Domain, Jiang et al., 1997; O'Rourke et al., 1999; Ema et al., 1999; Carrero et al., 2000; Gu et al., 2001). The final C-terminal 50 amino acids of HIF-1α and HIF-2α show strong sequence homology (60% identity), while the preceding 50 amino acids are divergent. Chimeric proteins containing the CADs fused to the Gal4 DNA binding domain show the CADs are silent during normoxia, but potently induced during hypoxia (FIGS. 3A & B). The Fe(II) chelator 2,2'-dipyridyl (DP), a known hypoxia mimetic that activates full length HIF-1α and HIF-2α, also induces activity of the CADs. The large increases in activities shown in FIG. 3 are consistent with work by others, who like us, also find that hypoxia or hypoxia mimetics do not influence protein levels of the CADs (FIG. 4B and Jiang et al., 1997; O'Rourke et al., 1999; Ema et al., 1999; Carrero et al., 2000; Gu et al., 2001)).

Figure 4:
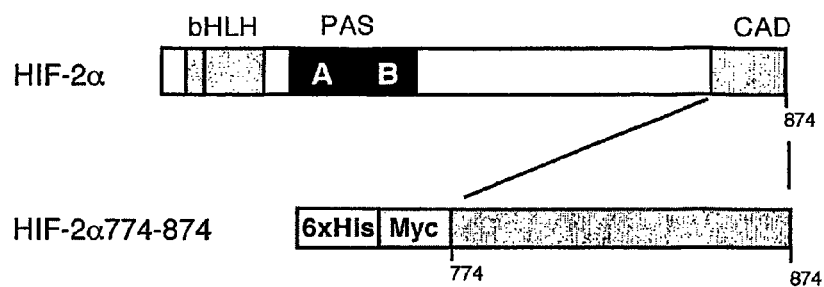
FIG. 4. A) Schematic showing domains of HIF-2α and the construct containing the CAD region fused to a 6xHis tag/myc epitope which was used to generate a stable expressing cell line. B) Protein expression of the HIF-2α CAD is not increased by hypoxia or DP treatment. Stable transfected HEK 293T cells were incubated at normoxia or subjected to hypoxia or DP for 3 h, after which whole cell extracts (20 µg) were separated by SDS-PAGE and analysed by immunoblotting with a 9E10 anti-myc monoclonal antibody. The 293T control lane contains extract from cells stably transfected with blank expression vector. C) Sypro-Ruby (Bio-Rad) stained SDSPAGE gel showing an example of HIF-2α CAD purified from stable transfected cells. Extracts from non transfected cells subjected to the same purification procedure lack the HIF-2α CAD band.The higher molecular weight contaminant that is co-purified by the procedure was identified as 60S ribosomal protein L27A by mass spectrometry.
Figure 4:
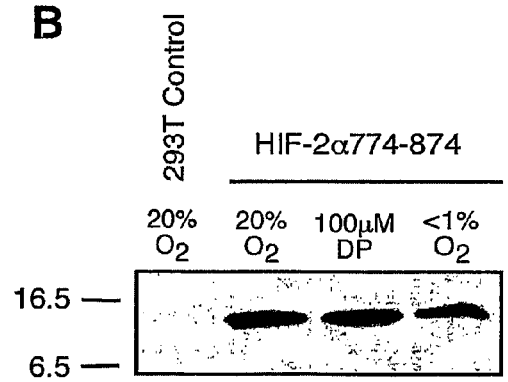
Figure 4:
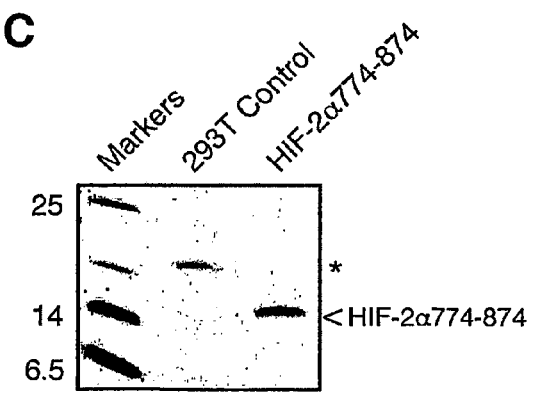
Figure 5:
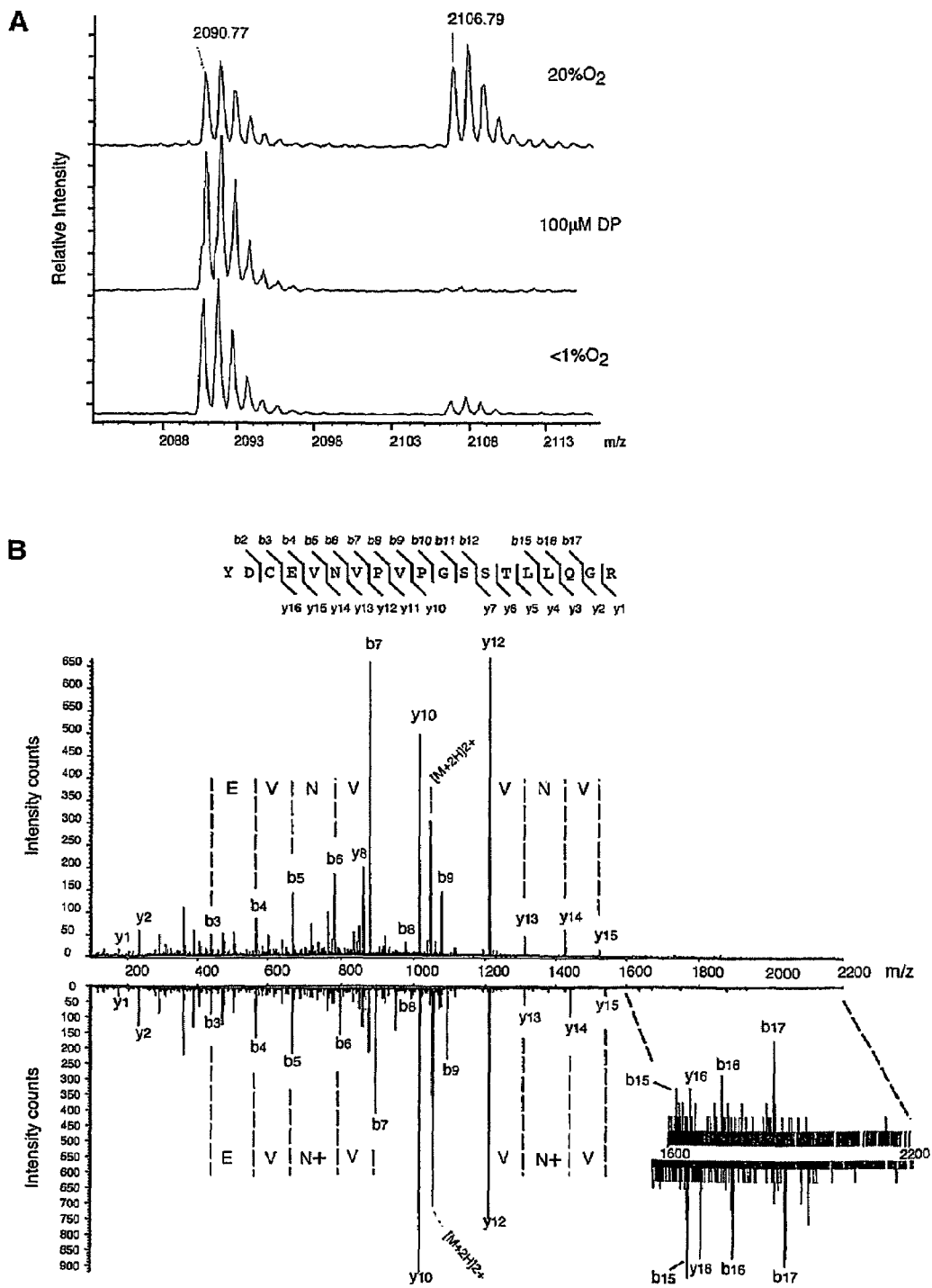
FIG. 5. A) Mass spectrometry of the HIF-2α CAD purified from cells incubated in normoxia or subjected to hypoxia (<1% $O_2$, 3 h) or DP (100 µM, 3 h) treatments. A & B) Magnified views of the MALDI-TOF spectra corresponding to hydroxylation (+16 Da) of the peptide YDCEVNVPVPGSSTLLQGR [SED ID NO. 1], which appears in the normoxic but not hypoxic or DP treated samples. B) Analysis of fragment ions resulting from tandem MS/MS sequencing of the hydroxylated and non-hydroxylated forms of the peptide shows the hydroxylated residue to be Asn851. For instance, fragment ions, characterized by the b- and y-type ion nomenclature for peptide fragmentation were observed with the unmodified (non-hydroxylated) peptide that covered nearly the entire peptide sequence (upper panel). The modified (hydroxylated) peptide produced some fragment ions (lower panel) at the same m/z values as the unmodified peptide, these coincidental fragments corresponded to portions of the sequence that did not contain Asn851. Fragments were also observed for the modified sequence at m/z values of +16 Da higher than Asn851-containing fragments of the unmodified sequence. The boundary of the coincident and +16 Da fragment ions is indicated by the symbol N+ on the fragment ion spectrum of the modified sequence.

To explore the mechanism of hypoxia induced activation of the CADs we engineered stable cell lines to express the C-terminal 100 amino acids of HIF-2α (FIG. 4). The HIF-2α fragment was purified to near homogeneity from normoxic cells, or cells subjected to either hypoxia or DP treatment (FIG. 4C). To identify possible posttranslational modifications involved in activation of transcription, purified samples were subjected to MALDI mass spectrometry. Analysis of fragments derived from tryptic digestion revealed that one peptide from the normoxic sample, corresponding to the sequence 846-YDCEVNVPVPGSSTLLQGR-864 [SEQ ID NO. 1], contained a form with a mass 16 Da above the predicted mass (FIG. 5A). The +16 increase indicates the presence of an hydroxyl group on one of the amino acids. Analysis of the same peptide derived from DP treated cells showed a complete lack of the +16 mass increase, while the peptide from hypoxia treated cells showed near abrogation of the +16 peak (FIG. 5B). Tandem mass spectrometry sequencing of the peptide derived from normoxic cells established that the asparagine 851 was hydroxylated (FIG. 5C). In contrast, the conserved proline 853 residue, which might be suspected to undergo oxygen dependent hydroxylation by the prolyl hydroxylase that modifies the ODD, was unchanged in this sample (FIG. 5C).

Figure 6:
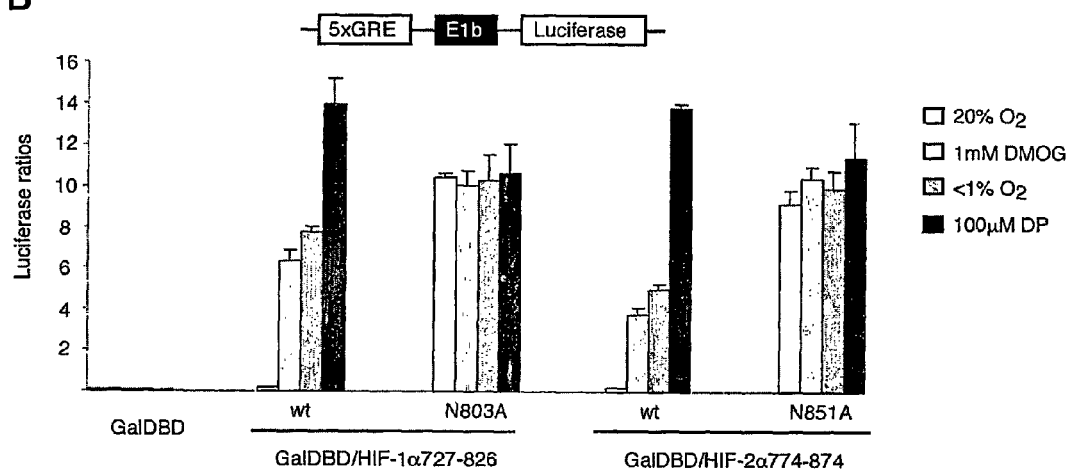
FIG. 6. Mutation of asparagine confers strong, constitutive activity to the HIF-1α and HIF-2α CADs. A) Sequence comparisons show conservation of the critical Asn between HIF-1α and HIF-2α across species. B) Reporter gene assays showing constitutive activity of the mutants Gal4DBD/HIF-1α 727-826(N803A) and Gal4DBD/HIF-2α 774-874(N851A). HEK293T cells were transfected according to the protocol of FIG. 3A and data represent the average of triplicate transfections +/standard deviation. (C). The wild type and mutant Gal4DBD/HIF chimeras used in A) are expressed at the same levels during transient transfection. Whole cell extracts of control or transfected cells were separated by SDS-PAGE and proteins detected by immunoblotting with antibodies directed against the C-terminus of HIF-1α (C) or HIF2α.
Figure 6:
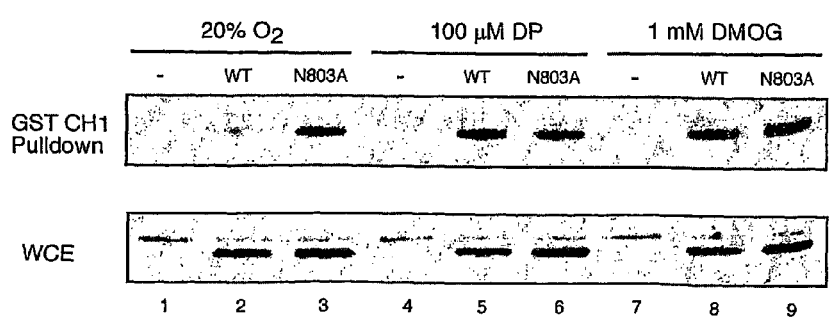

Asparagine 851 is well conserved across species for HIF-2α, as is the equivalent Asn 803 in HIF-1α (FIG. 6A), implying that loss of hydoxylation of this residue may underlie the hypoxic switch that invokes activity of the CADs. An enzyme that has the ability to hydroxylate aspartic acid and asparagine residues has been described, and like the prolyl hydroxylases, is a member of the oxygen, Fe(II) and 2-oxoglutarate dependent family of enzymes. If an asparaginyl hydroxylase of this type is responsible for silencing the CADs during normoxia, its activity in cells should be blocked by dimethyl-oxalylglycine (DMOG), a cell permeable analog of 2oxoglutarate that functions as a competitive inhibitor for this class of enzymes (Jaakkola et al., 2001). Treatment of cells with DMOG resulted in activation of the Gal4DBD/HIF-1α and Gal4DBD/HIF-2α CAD chimeras to a similar extent as that seen during treatment with hypoxia (FIG. 6B). Moreover, mutation of the critical Asn residues to alanine, ie N803A in HIF-1a and N851A in HIF-2α, provided the Gal4DBD chimeras with full transcriptional activities. These activities were not increased by treatment with hypoxia, DP or DMOG (FIG. 6B) and expression levels of wild type and mutant chimeras are identical during the transient transfection process (FIG. 6C). The point mutants provide strong evidence that hydoxylation of the critical asparagines mediate silencing of the HIF-1α and HIF-2α transactivation domains. In contrast, mutation of the conserved proline within this region to alanine, ie P805A in HIF-1α and P853A in HIF-2α, resulted in complete loss of activities of the HIF-1α and HIF-2α CADs during both normoxia and hypoxia (data not shown).

These results reveal that two related but distinct processes underpin the oxygen sensing mechanism for the hypoxia inducible factors. During normoxia, oxygen dependent prolyl and asparaginyl hydroxylases modify critical residues in the ODD and CAD regions respectively, inhibiting function by conferring lability and transcriptional silencing to the proteins. When the oxygen concentration becomes limiting, activities of these enzymes is attenuated to allow increases in both HIF protein levels and intrinsic transcriptional potency. Importantly, overexpression of the HIF-1α CAD in transgenic mice has been shown to attenuate tumour development, presumably by interrupting function of the endogenous HIF-1α CAD (Kung et al., 2000).

Prolyl hydroxylases that modify the ODD have recently been found. (Bruik and McKnight, 2001) These are novel prolyl hydroxylases that differ from the collagen prolyl hydroxylases described thus far that are located in the lumen of the ER. Likewise, the HNH (FIH-1) protein we reveal to be a novel asparagine hydroxylase that differs from the aspartyl/asparaginyl β-hydroxylase that modifies residues within a motif known as the EGF-like domain (Jia et al., 1994; Dinchuk et al., 2000). Consensus residues within the EGF-like domain bear no resemblance to any sequences within HIF-1α and HIF-2α, consistent with the idea that any FIH-1 related HNH enzymes that modifty the CADs are likely to be novel members of the 2-oxolutarate dependent family of dioxygenases. Finally, no function for hydroxylated Asp/Asn residues within the EGF-like domains known to be targeted by the characterised aspartyl/asparaginyl β-hydroxylase has been described. The instant work presents a novel posttranslational modification for control of a transactivation domain and is the first to ascribe a function, that of transcription silencing, for hydroxylation of asparagine residues.

REFERENCES

Bruick, R. K. and McKnight, S. L. (2001) *Science.* 294, 1337-1340
Carrero et al., (2000) *Mol. Cell. Biol.* 20, 402
Dinchuk et al., (2000) *J. Biol. Chem.* 275, 39543
Ema et al., (1997) *Proc. Natl. Acad. Sci. U.S.A.* 94, 4273
Ema et al., (1999) *EMBO J.* 18, 1905
Gorman et al., (1996). *Rapid Commun. Mass Spectrom.* 10: 529-536
Gorman et al., (1997). *Protein Sci.* 6:1308-1315
Gothie et al., (2000) *J. Biol. Chem.* 275, 6922
Gu et al., (2001) *J. Biol. Chem.* 276, 3550
Ivan et al., (2001)*Science* 292, 464
Iyer et al., (1997) *Genes Dev.* 12, 149
Jaakkola et al., (2001)*Science* 292 468
Jia et al., (1994) *Proc. Natl. Acad. Sci. U.S.A* 91, 7227
Jiang et al., (1997)*J. Biol. Chem.* 272, 19253
Kung et al., (2000) *Nature Medicine* 6, 1335
Lando et al., (2002) *Science* 295, 858
Lando, et al., (2002) *Genes Dev.* 16, 1466-1471
Lopaticki et al., (1998). *J. Mass. Spectrom.* 33, 950-960
Mahon et al., (2001). *Genes Dev* 15:2675
Morwenna Wood et al., (1998) *J. Biol. Chem.* 273, 8360
O'Rourke et al., (1999) *J. Biol. Chem.* 274, 2060
Peng et al., (2000) *Proc. Natl. Acad. Sci. U.S.A.* 97, 8386
Pitt et al., (2000). *J. Biol. C12em.* 275: 6469-6478
Ratcliffe et al., (1998) *J. Exp. Biol.* 201; 1153-1162
Ryan et al., (1998) *EMBO J.* 17, 3005
Semenza, (2000) *Genes Dev.* 14, 1893
Tian et al., (1997)*Genes Dev.* 11, 72
Tian et al, (1998) *Genes Dev.* 12, 3320
Zhang, J. H et al., (1999) *Anal. Biochem.* 271, 137
Zhu and Bunn (2001) *Science,* 292, 449-51

The invention claimed is:

1. A method of screening for agonists or antagonists of an asparagine hydroxylase capable of hydroxylating a target asparagine, the asparagine hydroxylase being FIH (Factor Inhibiting Hypoxia Inducible Factor);

the method including the steps of:
  i) contacting with a preparation containing FIH, under conditions suitable for hydroxylation, a peptide or protein comprising the target asparagine and including a hydroxylation motif of amino acids necessary for hydroxylation by the asparagine hydroxylase, said hydroxylation motif being selected from the group consisting of SEQ ID NO: 4 and SEQ ID NO: 5
  ii) additionally contacting the mixture with a candidate agonist or antagonist, and
  iii) measuring directly or indirectly either inhibition or enhancement of hydroxylation of the target asparagine.

2. The method of screening for agonists or antagonists of the asparagine hydroxylase as in claim 1 wherein the protein or peptide has HIF (Hypoxia Inducible Factor) transactivation activity.

3. The method of screening for agonists or antagonists of the asparagine hydroxylase as in claim 2, the method step iii) further comprising a step of contacting a nucleic acid with the mixture, the nucleic acid encoding an indicator gene regulated by a promoter activatable by the transactivational activity, and the transactivational activity is measured by measuring the activity of the indicator gene.

4. The method of screening of agonists or antagonists of the asparagine hydroxylase as in claim 3 wherein the protein is a portion of a CAD (C-terminal transactivation domain) domain of either HIF (Hypoxia Inducible Factor) 1α or HIF 2α.

5. The method of screening for agonists or antagonists of the asparagine hydroxylase as in claim 3 wherein the indicator gene is Gal 4 (gene encoding galactose-specific transcription enhancing factor).

6. The method of screening for agonists or antagonists of the asparagine hydroxylase as in claim 1 wherein the inhibition or enhancement of hydroxylation of the target asparagine is measured directly by analysis of the target asparagine.

7. The method of screening for agonists or antagonists of the asparagine hydroxylase as in claim 1 wherein the analysis is by mass spectrometry.

8. The method of screening for agonists or antagonists of the asparagine hydroxylase as in claim 6 wherein the analysis is by a carbon dioxide capture assay.

9. The method of screening for agonists or antagonists of the asparagine hydroxylase as in claim 6 wherein the protein or peptide consists of a portion of a HIF (Hypoxia Inducible Protein) protein, the portion of HIF protein including the hydroxylase binding motif and the hydroxylation motif but not having transactivational activity.

10. The method of screening for agonists or antagonists of the asparagine hydroxylase as in claim 1 wherein the protein or peptide includes an apsparagine hydroxylase binding motif of amino acids necessary for binding of the asparagine hydroxylase and the protein or peptide comprises HIF transactivational activity, and the method includes the further steps of
  iv) screening the candidate agonist or antagonist for capacity to inhibit or enhance transactivational activity, and
  v) measuring the extent of inhibition or enhancement of hydroxylation activity of the asparagine hydroxylase only if inhibition or enhancement of transactivational activity is exhibited.

11. The method of screening for agonists or antagonists of the asparagine hydroxylase as in 10 wherein the protein consists of a CAD domain.

12. The method of screening for agonists or antagonists of the asparagine hydroxylase as in claim 1 wherein the asparagine hydroxylase is used in purified form.

13. The method of screening for agonists or antagonists of the asparagine hydroxylase as in claim 4 wherein the indicator gene is Gal 4.

14. The method of screening for agonists or antagonists of the asparagine hydroxylase as in claim 10 wherein said binding motif is selected from the group consisting of SEQ ID NO: 6 and SEQ ID NO: 7.

15. The method of screening for agonists or antagonists of the asparagine hydroxylase as in claim 10 wherein the peptide or protein consists of the hydroxylase binding motif and the hydroxylation motif spaced apart by nine amino acids.

* * * * *

SEQUENCE LISTING

<160> NUMBER OF SEQ ID NOS: 8

<210> SEQ ID NO 1
<211> LENGTH: 19
<212> TYPE: PRT
<213> ORGANISM: Mus musculus
<220> FEATURE:
<223> OTHER INFORMATION: portion of HIF 2 alpha gene with asparagine
that is hydroxylated

<400> SEQUENCE: 1

Tyr Asp Cys Glu Val Asn Val Pro Val Pro Gly Ser Ser Thr Leu
 1               5                  10                  15

Leu Gln Gly Arg

<210> SEQ ID NO 2
<211> LENGTH: 51
<212> TYPE: PRT
<213> ORGANISM: Human
<220> FEATURE:
<223> OTHER INFORMATION: portion of HIF 1 alpha gene including
asparagine that is hydroxylated

<400> SEQUENCE: 2

Ser Asp Leu Ala Cys Arg Leu Leu Gly Gln Ser Met Asp Glu Ser
 1               5                  10                  15

Gly Leu Pro Gln Leu Thr Ser Tyr Asp Cys Glu Val Asn Ala Pro
                20                  25                  30

Ile Gln Gly Ser Arg Asn Leu Leu Gln Gly Glu Glu Leu Leu Arg
                35                  40                  45

Ala Leu Asp Gln Val Asn
                50

<210> SEQ ID NO 3
<211> LENGTH: 51
<212> TYPE: PRT
<213> ORGANISM: Mus musculatus
<220> FEATURE:
<223> OTHER INFORMATION: portion of HIF 2 alpha gene including
asparagine that is hydroxylated

<400> SEQUENCE: 3

Ser Gly Val Ala Ser Arg Leu Leu Gly Pro Ser Phe Glu Pro Val
 1               5                  10                  15

Leu Leu Pro Glu Leu Thr Arg Tyr Asp Cys Glu Val Asn Val Pro
                20                  25                  30

Val Pro Gly Ser Ser Thr Leu Leu Gln Gly Arg Asp Leu Leu Arg
                35                  40                  45

Ala Leu Asp Gln Ala Thr
                50

<210> SEQ ID NO 4
<211> LENGTH: 17
<212> TYPE: PRT
<213> ORGANISM: Human
<220> FEATURE:
<223> OTHER INFORMATION: putative asparagine hydroxylation motif of HIF
1 alpha gene

<400> SEQUENCE: 4

Thr Ser Tyr Asp Cys Glu Val Asn Ala Pro Ile Gln Gly Ser Arg
 1               5                  10                  15

Asn Leu

<210> SEQ ID NO 5
<211> LENGTH: 17
<212> TYPE: PRT
<213> ORGANISM: Mus muscularus
<220> FEATURE:
<223> OTHER INFORMATION: putative asparagine hydroxylation motif of HIF
      2 alpha gene

<400> SEQUENCE: 5

Thr Arg Tyr Asp Cys Glu Val Asn Val Pro Val Pro Gly Ser Ser
 1               5                  10                  15

Thr Leu

<210> SEQ ID NO 6
<211> LENGTH: 8
<212> TYPE: PRT
<213> ORGANISM: Human
<220> FEATURE:
<223> OTHER INFORMATION: Putative asparagine hydroxylase binding motif
      of HIF 1 alpha gene

<400> SEQUENCE: 6

Ala Cys Arg Leu Leu Gly Gln Ser
 1               5

<210> SEQ ID NO 7
<211> LENGTH: 8
<212> TYPE: PRT
<213> ORGANISM: Mus muscularus
<220> FEATURE:
<223> OTHER INFORMATION: Putative asparagine hydroxylase binding motif
      of HIF 1 alpha gene

<400> SEQUENCE: 7

Ala Ser Arg Leu Leu Gly Pro Ser
 1               5

<210> SEQ ID NO 8
<211> LENGTH: 2825
<212> TYPE: DNA
<213> ORGANISM: Ovis aries
<220> FEATURE:
<223> OTHER INFORMATION: K2.10 Promoter sequence

<400> SEQUENCE: 8
aagcttgctg aggcggcttg attgcctcat aaagctgtcg ggctattttc tgctcacacg      60
aggatgatac ttcacagcca atgctcactg acccttggca aggtcctgct ggtccctgtt     120
agtatacagt gtaggggga gcacctcctg cctccaagca tgctcctcat cctcccaata      180
ttccagcaaa gtctggattg cattcatatt ttacagataa ggaatctggg aagcataact     240
tatcacaggt cacaaagcta gtaagtggca gagccaagct gccaacagtg cttttcatct     300
ccagagtcta cgctcccatc aggaccggga cctgggtaca ctcacggctc ccccaaccca     360
aggagatggg tgtgtctaca cagagaccct cagtgaagag tacagtttgg ataccgagcc     420
cactggatcc aggtagatga gcaggatcag aggacagagg caattaggag tgtggcgaca     480
gatggaggat ccaccgtctt catccacagc atttgaccaa gaattaatct cacataacca     540
ttggacatac agtgagaaac ttccagaagc tcaccagttc cagctgagac aagaggagag     600
aaatatctgg ttgtgtgttg gcagatgttt gagtcagcaa gggctgagca agaaagtacc     660

| | |
|---|---|
| aaccagcaca cctcccaccg aatcacccc aaagtcccac tgggcattca gctggattca | 720 |
| gtcaccccca aactcctagg ctgcctcctg tgtgtctctc acagctgatg cccctatccc | 780 |
| acagaaccca ctccaggcac aggagtctgt ggaaatctgt gcctagggct caagaggagg | 840 |
| ggctgcgaag gtctattttc agctccgagt gtatgttgcc cagctccctg ccagatctcc | 900 |
| acagttcacc cattccctgc cctcccagaa tagatggccc ctccctcacc ctgggacata | 960 |
| actgaccact cacctgagag gtggtaggga gggcaaaagg tgaggctctg ggagaatgct | 1020 |
| tggaaggcta tttttagccc agactgggtc agcatttggt ggcagtgggt caggaaacag | 1080 |
| gttcatcaga ggagtcatcc tcaagtacaa agctgctcaa gagacatacg ctcggaaggg | 1140 |
| tttataggct cacattctca gattagggaa acctcctgtc tcagtcccat agtccaccca | 1200 |
| tcaaagtcat cagtggccca cctgcaaaag gagggggca aataaggga atttggcttt | 1260 |
| caggacagcc atatgaatcc cccacctctg ctcacccaag gattcctctg atgggaggac | 1320 |
| cacttcagga ctcttggtga caccacttca tggactcttg gtgacctccc ctacctccaa | 1380 |
| caccttttca ctcttccagt tgggcgcata cacaccgaca gtcatcactc agcttccctg | 1440 |
| ctaggaaact gaaggacttc caccccacca acatctgacc ccagctcaac ctgggcatta | 1500 |
| ggggcttcct cctacctgtg acctctcccc ttcccacagt gaacaagcct tggcatccct | 1560 |
| gggtccacgc caaccctctc ctacctccac atacctccag tctctgctgg attcccagga | 1620 |
| cctagcaagg tgcgtggctg gcactggata agaatgtacc gaatgaatga aagaactagt | 1680 |
| gatggcacgg tttccaaatc agaactgaac tccttcctcg tctcccacca accctagcct | 1740 |
| taccccaccc tggtcctcct taaacacacc tccaaggagg ctccctggat taatcctgca | 1800 |
| gctctggggt gttctgctct cactcctgcc cctggcccac cagtgtgtgc tcagttgctt | 1860 |
| cagtcgtgtc cgactctttg tgaccctttg gacactatgg acccaccaag ttcctctgtc | 1920 |
| catgggatt ctccaggcaa gaatgctgga gtgcgttgtc atccccttct ccaggggagc | 1980 |
| ttcctgaccc agcagtcaaa cctgcatctc ttaagtctcc tgcattggca ggcaggttct | 2040 |
| ttaccactag tgcctcctgg gaagcccacc agtagtgatg cctagaactc tgaagaacaa | 2100 |
| ccttggttct ctcctgaact ctctgactca ggttctccca tgtcccagtg gatgccccat | 2160 |
| ggctcctgcc ctcctaggaa tatccaaagt gcaggggtca tgctctctcc caaatctctc | 2220 |
| ccccaacccc catcacggaa taggctctgg gtaggaacag cttaagagaa gctcattttg | 2280 |
| acggtgaagg atgggacata ctttaagaga taaaggcaaa gaggcccata acgagaggtt | 2340 |
| gttcaggaca agccacccc tcatgggaca ggccaaccac tctaccccaa ggccaggtca | 2400 |
| taggtccagg gcccatggtc cagccctgtg ccttccagaa aaggatttgg ggaccaggct | 2460 |
| ctaccccagg tcactgcaac tatcgcctgc actcagagca tggagtccaa ctagatactt | 2520 |
| ctaggaggtc tccacttcca gtagcaatgg gagggggaga agaagctcgt aaacggcttt | 2580 |
| gaagatgaaa caggcctgag gccgagattg ttgacacagc tctactgaat aggcaaacag | 2640 |
| ttggctctta agaggccagg gtgatgccaa gccaataaaa tgcagctgtt gtctcttttgc | 2700 |
| tgccccttt actgccagct atcctggtgc ataaaagggc ctgccacagc tcagggagca | 2760 |
| caggcctttg gctcagtcct ctgccagctt ctccactgtc cagacacctc cctgtcgaca | 2820 |
| acatg | 2825 |